US009788897B2

(12) United States Patent
Neuberger (10) Patent No.: US 9,788,897 B2
(45) Date of Patent: Oct. 17, 2017

(54) METHOD AND DEVICE FOR UNDERSKIN RADIATION TREATMENT OF ADIPOSE TISSUE

(75) Inventor: Wolfgang Neuberger, Dubai (AE)

(73) Assignee: biolitec Unternehmensbeteiligungs II AG, Vienna (AT)

( * ) Notice: Subject to any disclaimer, the term of this patent is extended or adjusted under 35 U.S.C. 154(b) by 243 days.

(21) Appl. No.: 12/987,416

(22) Filed: Jan. 10, 2011

(65) Prior Publication Data

US 2011/0172652 A1  Jul. 14, 2011

Related U.S. Application Data

(60) Provisional application No. 61/293,376, filed on Jan. 8, 2010.

(51) Int. Cl.
A61B 18/22 (2006.01)
A61B 18/00 (2006.01)
A61B 18/20 (2006.01)

(52) U.S. Cl.
CPC ...... *A61B 18/22* (2013.01); *A61B 2018/0019* (2013.01); *A61B 2018/00994* (2013.01); *A61B 2018/2005* (2013.01); *A61B 2018/2272* (2013.01)

(58) Field of Classification Search
CPC ..... A61B 18/201; A61B 18/24–18/245; A61B 2018/2272; A61B 18/22; A61B 2018/225; A61B 2018/2005; A61B 2018/0019; A61B 2018/00589; A61B 2018/00607
USPC .............................................. 606/15, 14, 16
See application file for complete search history.

(56) References Cited

U.S. PATENT DOCUMENTS

| 4,418,688 | A | * | 12/1983 | Loeb .............................. 600/108 |
| 4,478,217 | A | * | 10/1984 | Shimada et al. ................. 606/13 |
| 4,729,373 | A | * | 3/1988 | Peyman ............................ 606/4 |
| 4,846,172 | A | * | 7/1989 | Berlin .............................. 606/4 |
| 5,139,494 | A | * | 8/1992 | Freiberg ............................ 606/3 |
| 5,242,438 | A | * | 9/1993 | Saadatmanesh ....... A61B 18/24 606/15 |
| 5,292,320 | A | * | 3/1994 | Brown et al. .................... 606/15 |
| 5,312,392 | A | * | 5/1994 | Hofstetter ............ A61N 5/0601 606/15 |
| 5,324,255 | A | * | 6/1994 | Passafaro et al. .............. 604/22 |
| 5,401,272 | A | * | 3/1995 | Perkins .......................... 606/15 |
| 5,431,646 | A | * | 7/1995 | Vassiliadis et al. ............. 606/6 |

(Continued)

*Primary Examiner* — Nathan J Jenness
(74) *Attorney, Agent, or Firm* — BJ Associates; Bolesh J. Skutnik (57) ABSTRACT

The device for carrying out underskin radiation treatment consists of a handpiece that allows easy manipulation by physicians, with a part that can be inserted below the skin and a part that can be held and manipulated outside the body. The part inserted below the skin can be vibrated or oscillated by means of suitable transducers to aid in distributing the radiation. Simultaneously or immediately afterwards, liquefied tissue is aspirated. If convenient, fluid irrigation of the area to be treated can be done. In a preferred embodiment, handpiece consists in a hollow cannula incorporating at least one channel for suction and/or irrigation and a light guiding means in its body/wall section for the purpose of the treatment and liquefaction of adipose tissue. The device further comprises at least one radiation source, included in device part affixed to the handpiece either in a permanent or detachable manner.

14 Claims, 8 Drawing Sheets

(56) References Cited

U.S. PATENT DOCUMENTS

| | | | |
|---|---|---|---|
| 6,071,276 A * | 6/2000 | Abela | 606/27 |
| 6,391,023 B1 * | 5/2002 | Weber et al. | 606/15 |
| 6,454,762 B1 * | 9/2002 | Rosler et al. | 606/15 |
| 7,306,588 B2 * | 12/2007 | Loeb et al. | 606/15 |
| 2005/0131400 A1 * | 6/2005 | Hennings | A61B 18/24 606/15 |
| 2009/0240242 A1 * | 9/2009 | Neuberger | 606/7 |
| 2009/0287198 A1 * | 11/2009 | Hanley et al. | 606/15 |

\* cited by examiner

METHOD AND DEVICE FOR UNDERSKIN RADIATION TREATMENT OF ADIPOSE TISSUE

DOMESTIC PRIORITY UNDER 35 USC 119(E)

This application claims the benefit of U.S. Provisional Application Ser. No. 61/293,376 by Wolfgang Neuberger, entitled "Method and Device for Underskin Radiation Treatment of Adipose Tissue" filed Jan. 8, 2010, which is incorporated by reference herein.

BACKGROUND OF THE INVENTION

1. Field of the Invention

The present invention is related to minimally invasive devices and methods for treatment of biological tissue. More particularly, the invention relates to underskin radiation treatment and removal of adipose tissue.

2. Invention Disclosure Statement

Nowadays, the abundance of readily available foods and sedentary lifestyle allow people to gain excessive weight by an increase in adipose tissue fat cells. Sometimes, this situation is enhanced due to certain hereditary conditions.

Excessive fat deposits or lipodystrophies are produced by a disproportionate increase in the deeper section of the subcutaneous cellular tissues. The only effective way to treat lipodystrophies is to directly act on the genetically altered fat tissues and similar tissues in the treatment area.

Historically, different methods have been developed to treat this condition, i.e., direct liposuction, ultrasonic liposuction, vibrational liposuction, laser lipolysis, laser lipolysis and suction and simultaneous laser lipolysis and suction.

Direct liposuction consists of the introduction into the adipose layers of probes roughly 5 mm in diameter through holes made in the skin of the patient undergoing treatment, for suction and removal of fat. This technique has a number of disadvantages, such as the in-homogeneity created in the zone of insertion of the probe, as well as excessive bleeding. Furthermore, both the cells of fat and the stroma are aspirated non-selectively. Several deaths have been reported because of the crudity of conventional liposuction.

Ultrasonic liposuction utilizes subcutaneous ultrasonic probes to rupture the membrane of the adipose cells, thus causing the escape of liquid which has to be aspirated out subsequently by vacuum means, much like in direct liposuction. Liposuction by ultrasonic means also produces connective tissue damage, so bleedings might occur as well. Furthermore, the lack of homogeneity resulting from the treatment still remains as a disadvantage.

Vibration liposuction uses a vibrating handpiece with an extraction channel integrated. Tissue is extracted by vacuum means and can be removed faster in comparison with the before-mentioned methods. However, connective tissue is still damaged, thus bleeding and other long term problems can occur. Another disadvantage is that vibrations of the handpiece can stress a surgeon's wrist. Therefore, it becomes difficult for surgeon to do precise work (e.g. suturing) after some time of treatment.

Laser lipolysis uses energy from a laser beam to liquefy the cells of the adipose layer. The liquefied fat is then carried away naturally by the lymphatic system or it can be removed by compression of remaining tissue. In U.S. Pat. No. 5,954,710, Paolini et al. disclose a device for the removal of subcutaneous adipose layers which comprises a first laser source, an optical fiber for conveying the laser beam emitted by said first source and a hollow needle for guiding the fiber, the fiber ending in the vicinity of the end of the needle. Preferably, the laser source has a wavelength ranging from 750 nm to 2500 nm. Pulse energy level is about 100 mJ in 200 µs of pulse duration, during a treatment time of a few minutes. Liquefied tissue can be removed by suction but is preferably left in place in order to be drained by lymphatic system and by action of phagocytes. According to the energy values mentioned previously, a high power laser source is required to perform treatment, leading to tissue carbonization, which may result in longer recovery periods, unsatisfactory results and patient discomfort.

In U.S. Patent Publication No. 2006/0253112A1, Suarez et al. disclose a method and device for cosmetic surgery, especially fat reduction and collagen reformation, by means of a high power laser operating at about 980 nm. The cosmetic surgery method substantially reduces or removes localized lipodystrophies, and essentially reduces flaccidity (at least 50%, due to fibro elastic retraction) by localized laser heating of adipose tissue using an optical fiber inserted into a treatment area. High power laser energy is applied through an optical fiber for breakdown of fat cells walls releasing the cell fluid. The optical fiber may be held within a catheter-like device having a single lumen and may have a diffuser mounted on the tip to further apply heating to tissues surrounding the whole tip. A saline solution may also be inserted into the treatment site to aid in the heating of the fat cells and their eventual destruction as well as their removal. The pool of cell fluid in the area of treatment is removed by a combination of techniques including: body removal by absorption and drainage from the entry sites (minimizing trauma), direct force application by means of elastic bandages and external suction applied to the entry sites. According to Suarez et al., treatment with the 980 nm laser was efficient and more suitable than traditional liposuction on up to 80% of the patients. Once again, as high power laser source is used to perform treatment, tissue carbonization can easily occur, which may result in longer recovery periods.

In U.S. Patent Publication No. 2006/0224148 Cho et al. disclose a device and related method for the removal of subcutaneous adipose layers comprising a laser source; an optical fiber for conveying a laser beam emitted by the laser source; and a hollow cannula for guiding the fiber to the subcutaneous treatment area. The cannula has a curved portion at its distal end, where the curved portion can be shaped to roughly conform to the contour of the patient's body structure. In this way, laser irradiation to lower dermis is generally avoided in curved body portions. Furthermore, a radiation detector or a temperature sensitive material is applied to the surface of the skin above the treatment area, in order to limit skin damage. Here again, tissue carbonization is the main action principle of this treatment.

In described previous prior art, since tissue removal is mainly restricted to the lymphatic system and compression of remaining tissue, only a low volume of tissue can be extracted effectively. Furthermore, the removal of liquefied adipose tissue via the lymphatic system can be insufficient and at times dangerous. In addition, as high power laser sources are used to perform treatment, tissue carbonization can easily occur, which may result in longer recovery periods, unsatisfactory results and patient discomfort.

An improvement to the previously mentioned techniques is performing liposuction after laser lipolysis, by utilizing a laser source to liquefy adipose tissue and then removing this tissue by means of a vacuum source. This method enhances the amount of liquefied tissue removal in comparison to laser lipolysis alone. However, as the removal of tissue is done after lipolysis, an ultrasound post-treatment is often necessary for the extraction of remaining tissue, increasing treatment time and cost and adding complexity to the process.

Another approach for performing improved liposuction is the simultaneous lipolysis and tissue extraction technique, which utilizes a laser source to liquefy adipose tissue and an extraction means for tissue removal in a substantially simultaneous way. In U.S. Pat. No. 6,464,694, Massengill discloses a liposuction cannula having a source of aqueous solution, a laser source, and a suction source. Aqueous solution is released into an active area within the cannula, and laser energy is directed onto the aqueous solution within the active area to energize the water molecules. The energized (hot) water molecules naturally escape from the active area into the surrounding fatty tissue to break down the fatty tissue and release liquid fatty material, which is removed by aspiration via the cannula. As can be seen, the device used in this invention does not apply laser energy in a direct way, so the amount of energy delivered can be difficult to quantify and can lead to unspecific tissue radiation.

Other patents claim devices disclosing removal of fat, liquefied by means of direct laser energy. In U.S. Patent Publication No. 2007/0219540A1, Masotti et al. claim a device for skin tightening which comprises a hollow cannula that contains an optical fiber connected to a laser source. The cannula is inserted subcutaneously into a patient so that the end of the fiber is located within the tissue underlying the dermis. The source emits an output pulse that is conveyed by the fiber to the dermis, where the pulse causes collagen destruction and shrinkage within the treatment area. In U.S. Pat. No. 7,060,061, Altshuler et al. claim a device for targeting lipid-rich tissue where probe includes a cannula through which liquid fat formed as a result of the irradiation ablating tissue walls is removed. In U.S. Patent Publication No. 2008/0188835A1, Hennings et al. claim a handpiece and method of use for laser-assisted liposuction for inciting, disrupting, and removing cellulite and adipose tissue.

It can be seen in mentioned prior art, where tissue is removed by vacuum means, irradiation as well as aspiration is carried out by inserting needle lumen which serves as a channel both for conveying laser energy by means of inserting optical fiber and for aspirating excess tissue. As a consequence, effective lumen is reduced by the presence of optical fiber when lasing. Therefore fat tissue can clog hollow needle, rendering simultaneous irradiation and aspiration difficult or even impossible. Thus, in order to achieve an effective treatment, irradiation and aspiration should be done sequentially, also leading to a longer procedure. Another disadvantage is that, optical fiber is confined inside hollow cannula thus leading to numerous limitations. In first place, the laser beam that emerges is focalized on a small area and at higher energies it may carbonize the tip and the tissue. In second place, optical fiber used must have a frontal emission pattern, limiting treatment possibilities. Furthermore, they do not include means for irrigation of fat tissue in order to make the procedure more efficient.

Summarizing, as can be seen from afore-mentioned prior art, even when irradiation and suction can be performed practically simultaneously, conventional laser liposuction approaches utilize high laser energy sources for irradiation of tissue to be treated. For instance, in the previously mentioned patent by Paolini, laser energy of 100 mJ is delivered in pulses of 200 µs, resulting in the high power/pulse value of 0.5 KW. These techniques are aimed at applying most of this high energy directly on adipose tissue, which may result in tissue carbonization. Tissue carbonization leads to longer recovery periods, unsatisfactory results and patient discomfort. Furthermore, since irradiation and aspiration are carried out through the same channel, its effective lumen is reduced by the presence of optical fiber when lasing, leading to inefficient fat extraction. In addition, since optical fiber is confined inside hollow cannula, some limitations arise: small focalization area of the laser beam which may carbonize the tip and the tissue; optical fiber must have a frontal emission pattern, limiting treatment possibilities. Finally, they do not include means for irrigation of fat tissue in order to make the procedure more efficient.

Due to the disadvantages and deficiencies of current liposuction techniques, a need exists for a device that provides a fast and safe alternative to address their shortcomings.

OBJECTIVES AND BRIEF SUMMARY OF THE INVENTION

It is an objective of the present invention to provide a safe and effective method and device for underskin radiation treatment.

It is another objective of the present invention to provide a method and device to treat tissue by emitting radiation at such wavelengths and intensity levels to practically avoid or minimize carbonization in the main tissue components such as adipose and connective tissue and to enable effective coagulation of smaller blood vessels.

It is also an objective of the present invention to provide a method and device that further comprises irrigation of treatment area and removal of adipose tissue during/after irradiation.

It is an objective of the present invention to provide a means for vibrating or oscillating a specific portion of a handpiece.

It is still another objective of the present invention to provide a system for effective radiation liposuction treatment which minimizes bleeding, procedure risks, treatment crudity and time of surgery, as well as patient recovery time.

Briefly stated, a method and device for underskin treatment and removal of adipose tissue by means of a radiation energy source is disclosed. The method disclosed of radiation-assisted tissue improvement consists of inserting a device or part of a device below the skin into areas to be treated, emitting radiation and moving the device within targeted tissue area to reach all parts. The method is characterized by emitting radiation at intensity levels low enough to substantially avoid or minimize carbonization in the main tissue components such as fat and connective tissue but at sufficient intensity to enable coagulation of smaller blood vessels thus preventing from bleeding at the wavelengths emitted. Thus, in preferred embodiments, power density is kept at up to about 2 W/mm. This allows for use of small diameter fibers such as 400 µm or less. The device for carrying out underskin radiation treatment consists of a handpiece that allows easy manipulation by physicians, with a part that can be inserted below the skin and a part that can be held and manipulated outside the body. The part inserted below the skin can be vibrated or oscillated by means of suitable transducers to aid in distributing the radiation. Simultaneously or immediately afterwards, liquefied tissue is aspirated. If desired, fluid irrigation of the area to be treated is done. In a preferred embodiment, handpiece consists in a hollow cannula incorporating at least one channel for suction and/or irrigation and a light guiding means in its body/wall section for the purpose of the treatment and liquefaction of adipose tissue. Due to handpiece's special configuration, a wide variety of fiber tip configurations can be used, i.e. side emitting, conical, radial emitting, drop shaped, reflective caps, but not limited thereto. Each fiber tip configuration allows for optimally performing different specific treatments. The device further comprises at least one radiation source, included in device part affixed to the handpiece either in a permanent or detachable manner.

The above and other objects, features and advantages of the present invention will become apparent from the following description read in conjunction with the accompanying drawings, (in which like reference numbers in different drawings designate the same elements).

DETAILED DESCRIPTION OF PREFERRED EMBODIMENTS

Most of the limitations and problems of previously mentioned techniques can be overcome by a controlled power laser liposuction technique, which utilizes a controlled power laser source to liquefy adipose tissue. This technique, as explained further below, presents some important advantages compared to previous methods, i.e., safer procedures, minimum or no tissue carbonization, possibility of using fibers of smaller diameter, minimal bleeding and consequently shorter patient recovery time and less patient stress and discomfort. Furthermore, the special configuration of the disclosed handpiece, also represents important advantages over prior art, i.e., channel for tumescence, irrigation or aspiration is not clogged up by the fiber, consequently increasing effective lumen; optical fiber can illuminate as well as emit radiation from a longer zone and with different patterns, because it is not confined inside hollow cannula.

The present invention discloses a method and device which allows for a safer and more effective liposuction treatment, by means of a controlled power laser radiation source.

Figure 1:
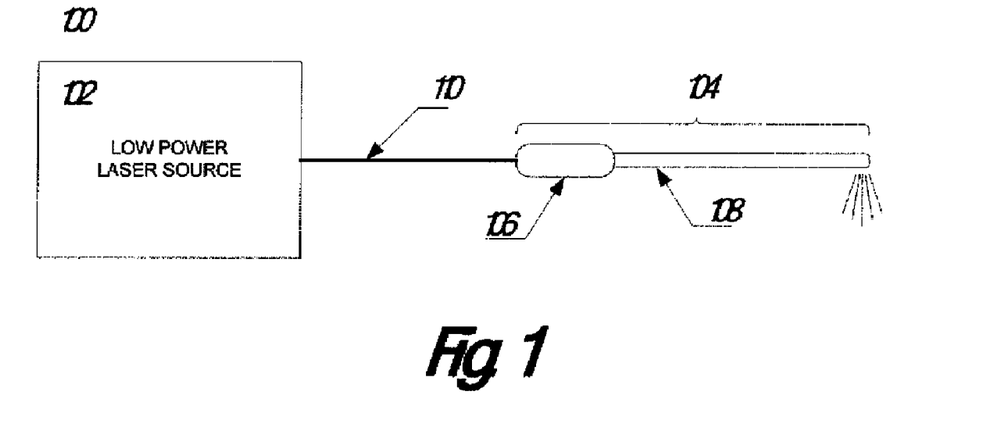
FIG. 1 depicts an embodiment of a laser delivery device including a controlled power laser source and a handpiece.

FIG. 1 depicts a schematic embodiment of laser delivery device 100, including CI controlled power laser source 102, optical fiber 110 which conveys radiation to handpiece 104. Handpiece 104 comprises maneuvering handle 106 and underskin insertion portion 108. Optical fiber 110 is locked to handpiece 104, thus solidarizing both in order to perform an efficient treatment. Underskin insertion portion 108 of handpiece 104 is inserted into a treatment area. Then, laser radiation is emitted to the tissue area through optical fiber 110, preferably a side emitting fiber. While irradiating, underskin insertion portion 108 of handpiece 104 is moved around inside tissue in order to reach all parts to be treated. If a side emitting fiber is used, radiation is aimed at adipose tissue, thus avoiding undesired irradiation to the underskin components. Laser source is characterized by emitting radiation at intensity levels low enough to practically avoid or minimize carbonization in the main tissue components such as fat and connective tissue but at sufficient intensity to enable coagulation of smaller blood vessels, thus preventing from bleeding at the spectrum emitted. Preferably, power density applied to treatment tissue is equal to or lower than 10 W/cm$^2$ and total power is no higher than 3 W. At such power levels, there is a wider variety of fiber sizes available to carry out the treatment. For example optical fibers with core diameters of 400 µm or below and overall dimensions below 1 mm can be used, as compared to the more common 600 µm or larger core diameter fibers with jacketed dimensions of over 1.5 mm. In preferred embodiments, radiation wavelength is in the range of 800 to 1100 nm, most preferably 980±40 nm. In other preferred embodiments, other single or combined radiation wavelengths are used, such as 1470±60 nm and 1940±60 nm.

Figure 2:
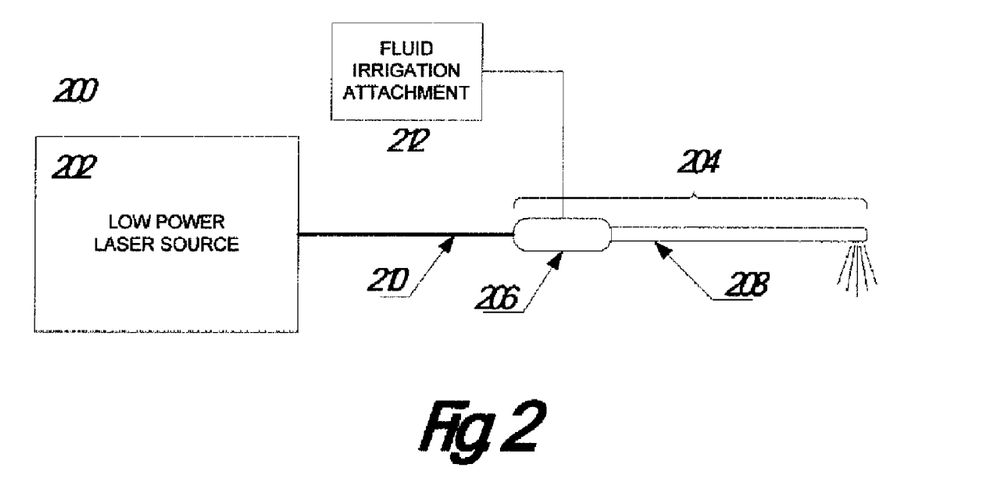
FIG. 2 shows an embodiment of a laser radiation device including a controlled power laser source, a fluid irrigation attachment and a handpiece.

FIG. 2 shows a schematic embodiment of laser delivery device 200, including controlled power laser source 202, fluid irrigation attachment 212 and optical fiber 210 which conveys radiation to handpiece 204. Handpiece 204 comprises maneuvering handle 206 and underskin insertion portion 208. Previous to inserting underskin portion 208 of handpiece 204, a specific fluid is irrigated in treatment area by means of fluid irrigation attachment 212. Irrigated fluid is usually an aqueous solution. Once the fluid spreads over the region of interest, low power laser radiation is emitted to the tissue area through optical fiber 210, preferably a side emitting fiber, in the same way as explained previously. The irrigated fluid (flushing) increases procedure efficiency and helps to keep the tissue at a safe distance from the optical output surface (or surfaces) thus avoiding creation and adhesion of debris. Furthermore, flushing also helps to decrease the power density on the tissue to a low enough level so as to further reduce the possibility of carbonization. At the same time the irrigated fluid transports thermal energy to the fat and forms an emulsion, which subsequently aids in tissue removal as it is extracted.

Figure 3:
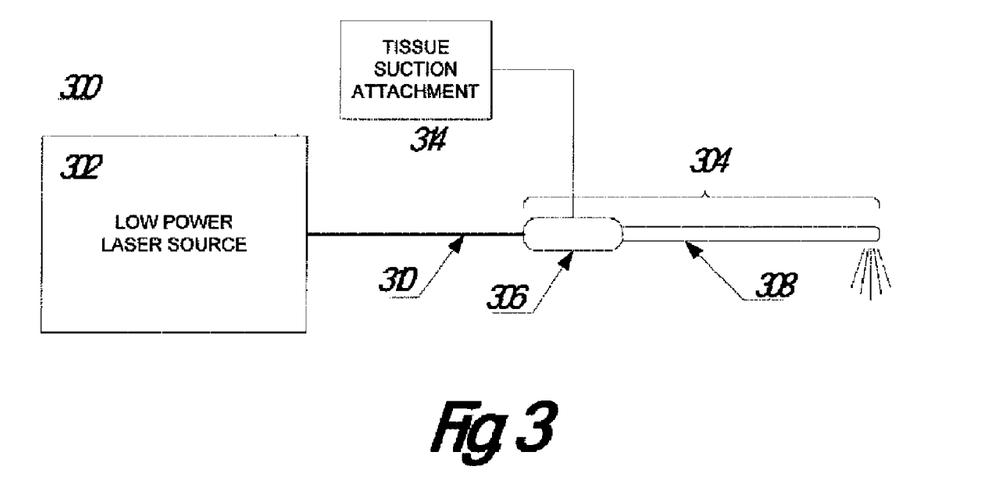
FIG. 3 shows an embodiment of a laser radiation device including a controlled power laser source, an adipose tissue suction attachment and a handpiece.

FIG. 3 shows a schematic embodiment of laser delivery device 300, including controlled power laser source 302, tissue suction attachment 314 and optical fiber 310 which conveys radiation to handpiece 304. Handpiece 304 comprises maneuvering handle 306 and underskin insertion portion 308. Underskin insertion portion 308 of handpiece 304 is inserted in treatment area. Then, low power laser radiation is emitted to the tissue area through optical fiber 310, preferably a side emitting fiber. While irradiating, underskin insertion portion 308 of handpiece 304 is moved around inside tissue in order to reach all sectors to be treated. During and/or after irradiation, liquefied adipose tissue can be extracted by means of tissue suction attachment 314.

Figure 4:
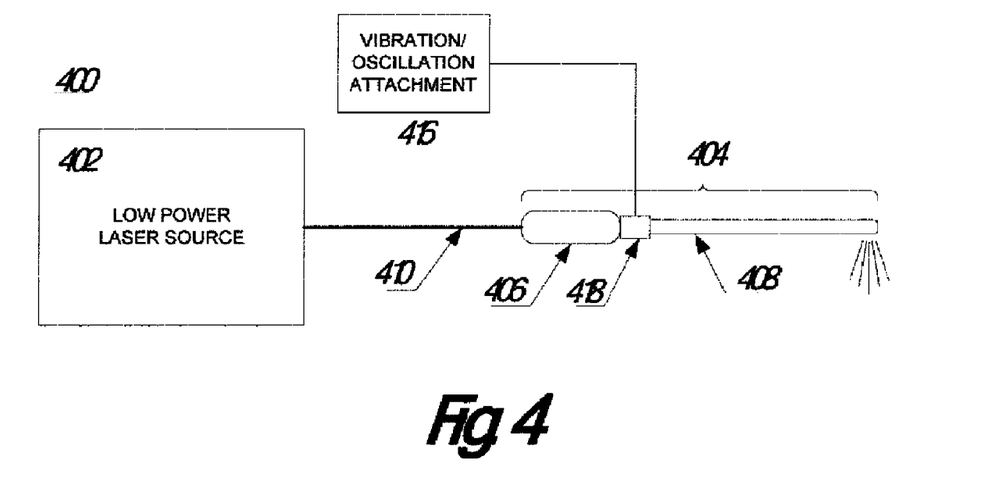
FIG. 4 depicts an embodiment of a laser radiation device including a controlled power laser source, a vibration/oscillation attachment and a handpiece.

FIG. 4 depicts a schematic embodiment of laser delivery device 400, including controlled power laser source 402, vibration/oscillation attachment 416, and optical fiber 410 which conveys radiation to handpiece 404 tip. Optical fiber 410 is inserted inside handpiece 404 so radiation is emitted at handpiece's distal end. When properly positioned, optical fiber 410 is locked to handpiece 404 in order to restrict their relative movement. Handpiece 404 comprises maneuvering handle 406, underskin insertion portion 408 and vibration/oscillation transducer 418. Underskin insertion portion 408 of handpiece 404 is inserted in treatment area. Then, low power laser radiation is emitted to the tissue area through optical fiber 410, preferably a side emitting fiber. While irradiating, underskin insertion portion 408 of handpiece 404 is moved around inside tissue in order to reach all sectors to be treated. Backward and forward movements of handpiece 404 are facilitated by vibrating/oscillating mechanical actuator 418, driven by vibration/oscillation source 416. Furthermore, this action enhances adipose tissue liquefaction. Vibration/oscillation transducer 418 produces its effect exclusively on underskin insertion portion 408 of handpiece 404, while maneuvering handle 406 remains substantially motionless. This can considerably diminish stress on clinician's wrist.

Figure 5:
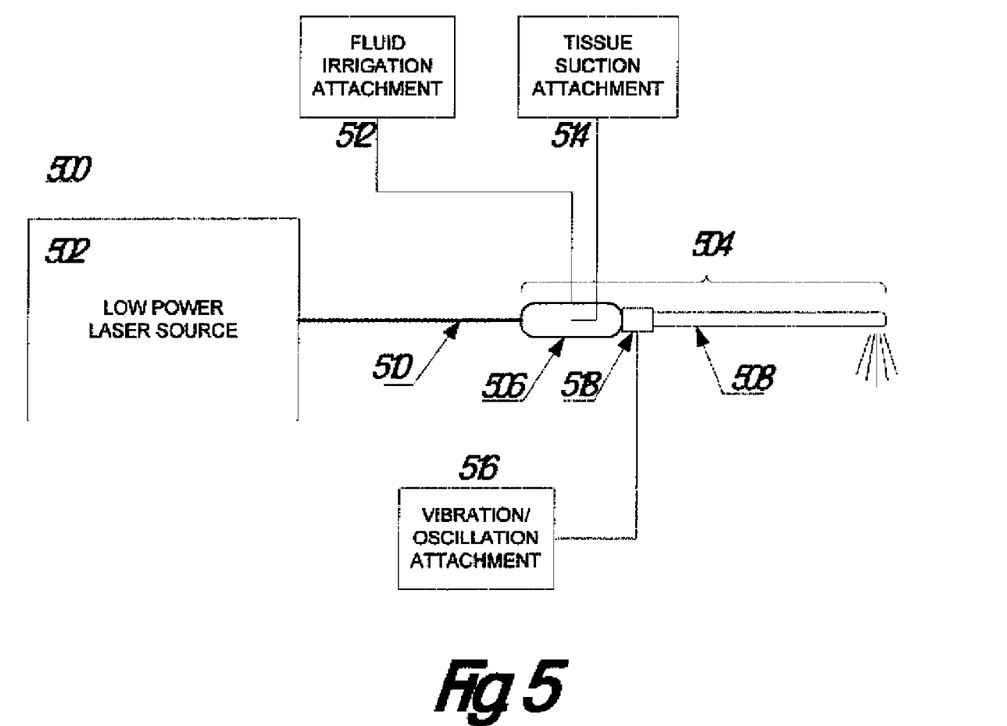
FIG. 5 shows an embodiment of a laser radiation device including controlled power laser source, fluid irrigation, adipose tissue suction and vibration/oscillation attachments and handpiece.

Constituent parts of previously described embodiments can be included in different configurations to achieve any desired combination. For instance, FIG. 5 depicts a schematic embodiment including all parts described in previous figures. Laser delivery device 500 comprises controlled power laser source 502, fluid irrigation attachment 512, tissue suction attachment 514 and vibration/oscillation source 516. It further includes handpiece 504, comprising three parts: maneuvering handle 506, underskin insertion portion 508 and vibration/oscillation actuator 518. The method disclosed in this embodiment consists of irrigating the tissue to be treated by means of fluid irrigation attachment 512, previous to or during irradiation. During irrigation, or once it is completed, underskin insertion portion 508 of handpiece 504 is inserted in treatment area. Laser radiation is emitted to the tissue area to be treated while underskin insertion portion 508 of handpiece 504 is moved around inside tissue in order to reach all sectors to be treated. Backward and forward movements of handpiece 504 are facilitated by vibrating/oscillating mechanical actuator 518, driven by vibration/oscillation source 516. While irradiating or once irradiation is finished, liquefied adipose tissue can be extracted by means of suction source 514.

Figure 6A:
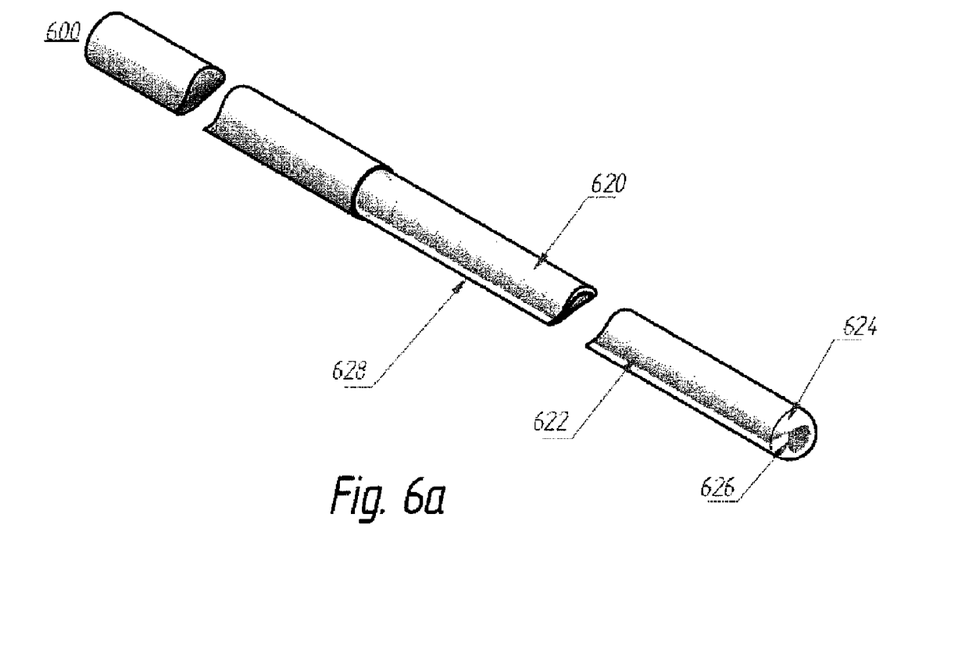
FIGS. 6a and 6b depict an embodiment of optical fiber set comprising a radial emitting fiber.
Figure 6B:
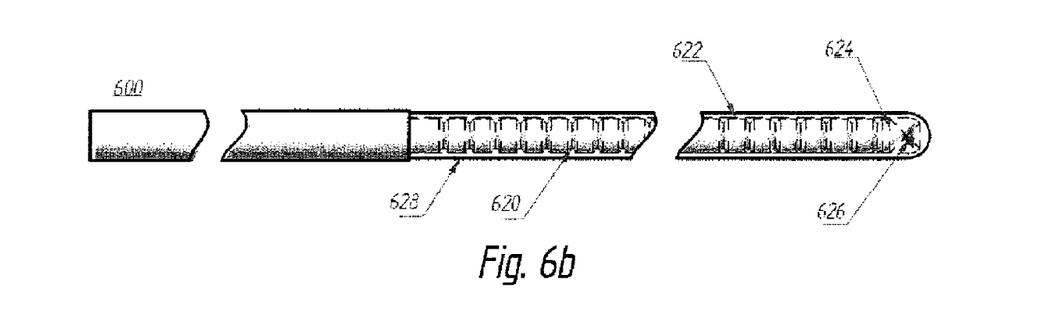

FIGS. 6a and 6b depict a preferred embodiment in which radial emitting optical fiber set 600 is used for treatment. Along the distal end section of the optical fiber core 622 there are one or more superficial grooves 620 which result in radial emission but also in longitudinal radiation transmission to optical fiber tip 624. The number of grooves and their relative spacing will depend on target tissue features, such as volume, location, etc. Optical fiber tip 624 has preferably a conical shape for achieving radial emission and placed opposite there is a preferably conical reflective surface 626 which enhances efficiency of radial emission by reflecting out any remnant forwardly transmitted energy in radial directions. Superficial grooves 620 allow for treating larger zones with an even heat distribution. This novel configuration enhances radial emission efficiency compared to prior art, as almost all radiation is radially emitted. Preferably, this assembly is surrounded by quartz cap 628, but also Teflon AF could be used. As an alternative of superficial grooves 620 and reflective surface 626, a diffuser tip or side firing fibers can also be used.

Figure 7A:
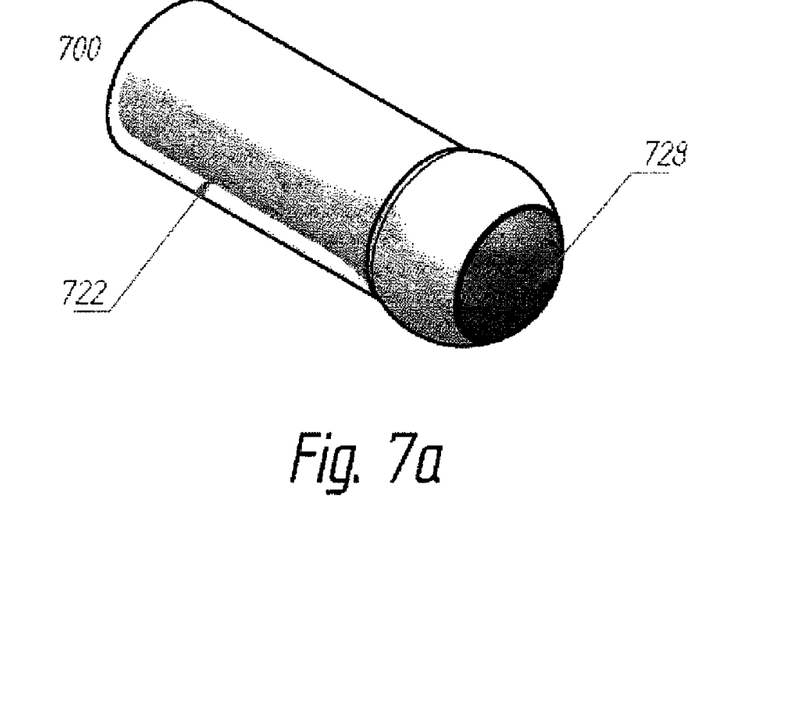
FIGS. 7a and 7b show an embodiment of optical fiber tip with a reflective cone.
Figure 7B:
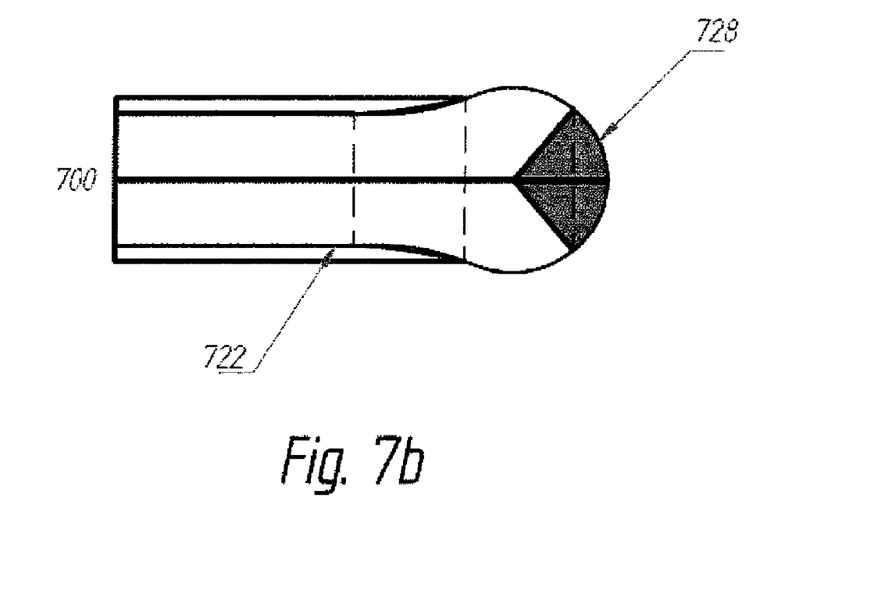

FIGS. 7a and 7b show a preferred embodiment in which radial emission is achieved by means of reflective cone 728 placed at optical fiber tip 700. In this embodiment, radiation transmitted through fiber core 722 is radially emitted when it reaches fiber tip. Due to this special configuration design, efficient radial emission is achieved.

Figure 8A:
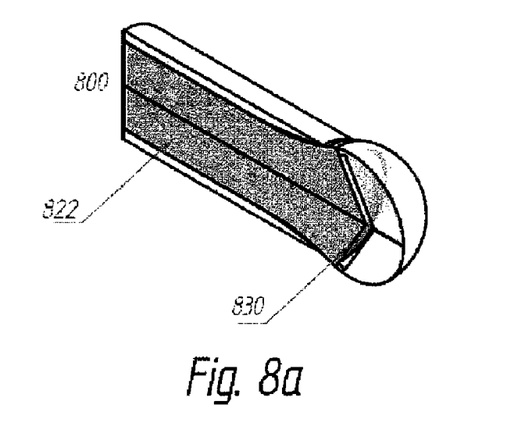
FIGS. 8a and 8b depict an embodiment of optical fiber tip with a reflective gap.
Figure 8B:
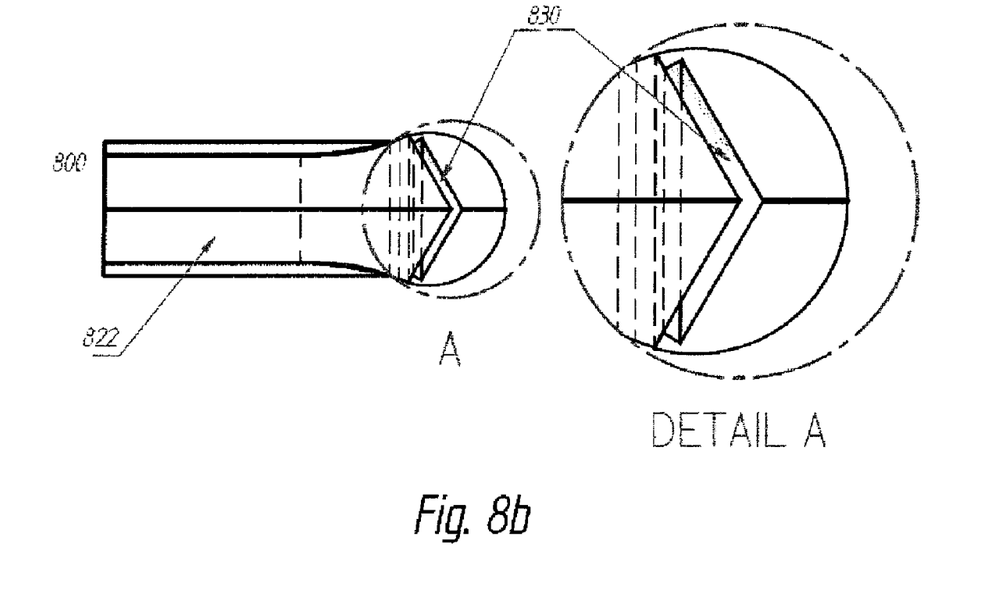

FIGS. 8a and 8b depict a preferred embodiment in which radial emission is achieved by means of reflective gap 830 placed at optical fiber tip 800. In this embodiment, radiation transmitted through fiber core 822 is radially emitted when it reaches fiber tip, as a consequence of the difference in refraction properties between gap and fiber core. Here again, this special configuration design leads to efficient radial emission.

Figure 9A:
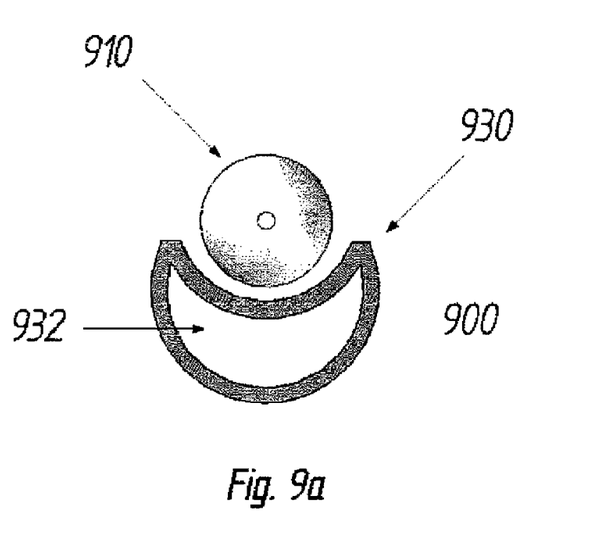
FIGS. 9a and 9b depict a schematic front and side view of handpiece in which optical fiber is attached to the outside of the cannula.
Figure 9B:
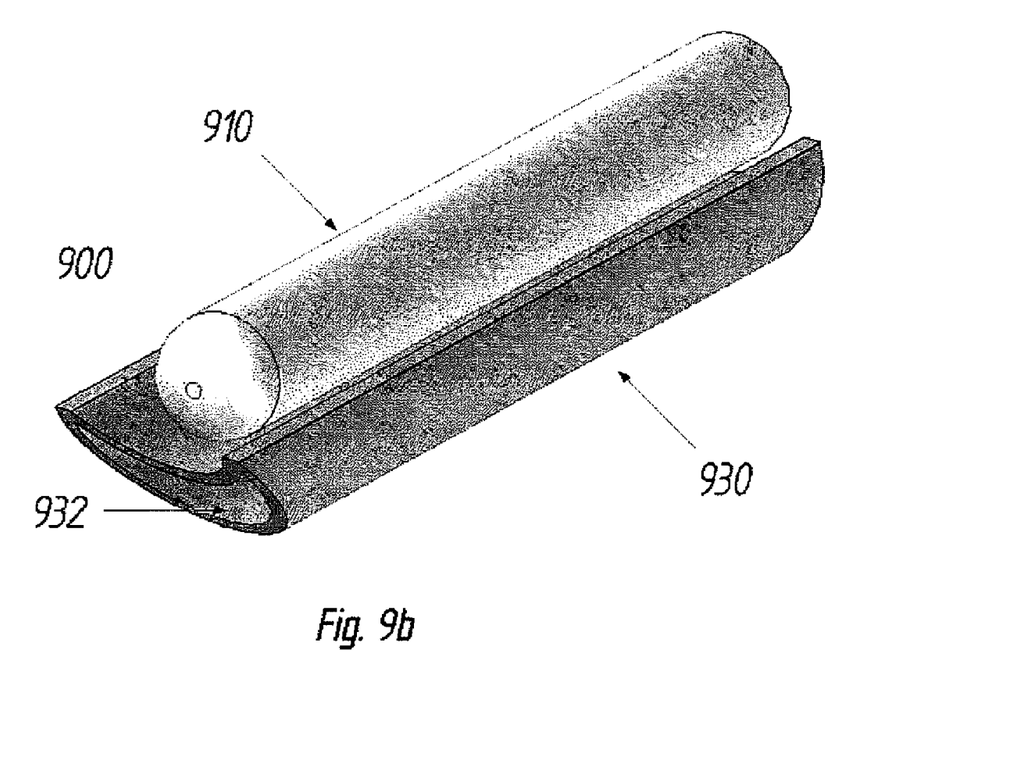

FIGS. 9a and 9b show a preferred embodiment of the present invention, in which handpiece 900 comprises optical fiber 910 attached to external wall of hollow cannula 930. Optical fiber 910 attachment can be achieved by mechanically snapping fiber in by means of a custom design or through other means. This feature represents an important advantage over prior art, because channel 932 for tumescence, irrigation or aspiration is not clogged up by the fiber 910, consequently increasing effective lumen. Another substantial advantage of this handpiece configuration is that optical fiber 910 can illuminate as well as emit radiation from a larger zone, because it is not confined inside hollow cannula. Consequently, spreading the beam out and irrigating the area to be treated helps to prevent tissue carbonization, as well as it improves visualization of treatment area. Furthermore, optical fiber with different radiation patterns (side fiber, bare fiber, radial fiber, etc.), can be used in order to achieve desired effects on tissue.

Figure 10:
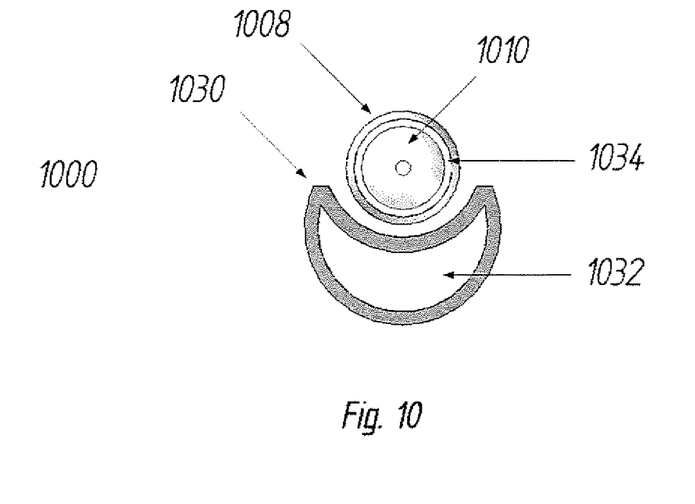
FIG. 10 shows a cross-sectional schematic drawing of handpiece with two channels, one for suction and another for irrigation.

FIG. 10 shows another preferred embodiment of the present invention in which handpiece 1000 is composed of two channels. Channel 1032 is preferable destined designed for suction and side tube 1034, which surrounds optical fiber 1010 and is attached to cannula 1030, is used for irrigation. As a consequence, simultaneous irrigation, radiation and suction can be performed efficiently. In another embodiment, cannula 1030 could be transparent or translucent or with multiple side-holes for a wider illumination area or better irrigation or tumescence.

In another embodiment, a system similar to that disclosed in U.S. Patent Publication 2006/0217692 A1 by Neuberger, can be used to control applied laser power. This can be useful to assure energy density applied is constant, thus preventing overheating tissue, for instance when hand movement is too slow or if it stops or hesitates. Likewise, surgeon can make sure enough energy density is applied to achieve desired tissue effect. For example, in laser liposuction, procedure consists in applying radiation through back and forth movements. By means of mentioned system, applied energy in each treatment spot is calculated by integrating the power emitted in that position along a time axis. While energy applied in each treatment spot is being calculated, an energy map of the treated zone is created in real time. As an advantageous consequence, more uniform and even treatment can be performed based on quantitative measurements and registers.

In another embodiment, a digital camera looking down on the treated area traces the treatment and picks up the radiation to create a treatment map. Surgeon can use this to control intervention when it is difficult to remember the extension of the treated zone.

In another preferred embodiment, laser radiation wavelength in a range between 500 and 700 nm is used.

In all previously described embodiments, laser radiation is preferably used, but not limited to that. LED or super luminescent radiation, having sufficient energy density, can also be used. Furthermore, other optical fiber tip designs can be used as radiation-conveying means. For instance, drop shaped optical fiber tip and handpiece can be used to achieve diffused emission, for irradiating large treatment areas. As another example, optical fiber can be bent at its distal end inside the handpiece, to achieve radiation to be emitted perpendicularly to the handpiece's main axis. This way, tissue surfaces that are normally difficult to reach can be treated easily.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A device for carrying out an underskin radiation-assisted tissue treatment comprising:
   a handpiece comprising:
      a distal part configured to be inserted into a tissue treatment site below the skin;
      a proximal part configured to be held and manipulated outside of a body;
      a first channel configured to provide fluid irrigation through the distal part; and
      a second channel formed by a hollow cannula and configured to provide suction through the distal part;
   at least one radiation source, which is either firmly affixed to the hand-piece or detachedly affixed to the handpiece;
   an optical fiber for lightguiding radiation from said source through the distal part of said handpiece to the tissue treatment site below the skin, the optical fiber comprising one or more superficial grooves having an annular configuration extending circumferentially around the optical fiber that are disposed along a distal end section of the optical fiber, the optical fiber being configured to longitudinally transmit radiation to a distal tip of the optical fiber and radially emit radiation by means of the one or more superficial grooves; and
   a reflective element disposed at the tip of the optical fiber for radially reflecting out radiation that is longitudinally transmitted to the tip of the optical fiber;
   wherein said first channel surrounds said optical fiber and said second channel partially surrounds said first channel, and said second channel is transparent or translucent to provide a wider irradiation area; and
   wherein the device is configured to provide simultaneous irrigation, irradiation and suction to the tissue treatment site below the skin.

2. The device according to claim 1, wherein said radiation source is selected from the group consisting of a laser, a diode laser, an LED, and a super luminescent diode.

3. The device as claimed in claim 1 wherein said radiation source further comprises sources operating at two or more wavelengths in combination, during a treatment.

4. The device according to claim 1, wherein said radiation source operates at a wavelength selected from the group consisting of 980±40 nm, 1470±60 nm, 1940±60 nm, and combinations thereof.

5. The device according to claim 1, wherein said radiation source operates at a wavelength between 800 nm to 1200 nm.

6. The device according to claim 5, wherein said radiation source operates at a wavelength of 980±40 nm.

7. The device according to claim 1, wherein said radiation source operates at a wavelength between 500 nm and 700 nm.

8. The device according to claim 1, wherein the superficial grooves are spaced apart along a longitudinal axis of the distal end section of the optical fiber.

9. The device according to claim 1, further comprising a cap surrounding the distal end section of the optical fiber.

10. The device according to claim 9, wherein in the cap is made of quartz.

11. The device according to claim 9, wherein in the cap is made of Teflon AF.

12. The device according to claim 1, further comprising a vibration component operatively connected to the handpiece and configured to vibrate the distal part of said handpiece when the distal part of said handpiece is inserted into the tissue treatment site below the skin during a treatment; backward and forward movement of the handpiece being facilitated by vibrations.

13. The device according to claim 12 wherein power density of said radiation at a tissue treatment site is no greater than 10 W/cm$^2$.

14. The device according to claim 13 wherein total power is no greater than 3 W.

* * * * *